(12) United States Patent
Ohtomo et al.

(10) Patent No.: US 8,759,474 B2
(45) Date of Patent: Jun. 24, 2014

(54) METHOD FOR PRODUCING LIQUID CRYSTAL POLYESTER

(75) Inventors: Shinji Ohtomo, Tsukuba (JP); Yusaku Kohinata, Tsukuba (JP); Hidehiro Kotaka, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 272 days.

(21) Appl. No.: 13/428,316

(22) Filed: Mar. 23, 2012

(65) Prior Publication Data

US 2012/0253060 A1  Oct. 4, 2012

(30) Foreign Application Priority Data

Mar. 29, 2011  (JP) .................................. 2011-072009

(51) Int. Cl.
 *C08G 63/02* (2006.01)
 *C07C 67/08* (2006.01)
 *C07C 67/10* (2006.01)
 *B32B 27/36* (2006.01)
 *C08G 63/06* (2006.01)

(52) U.S. Cl.
 CPC ............ *C08G 63/065* (2013.01); *C07C 67/08* (2013.01); *C07C 67/10* (2013.01); *B23B 27/36* (2013.01)
 USPC .............. 528/272; 560/80; 428/480; 528/274

(58) Field of Classification Search
 CPC ............................. C08G 63/02; C08G 63/065
 USPC .............................. 528/272; 428/480; 560/80
 See application file for complete search history.

(56) References Cited

U.S. PATENT DOCUMENTS

2003/0088053 A1* 5/2003 Ohbe et al. ................ 528/272

FOREIGN PATENT DOCUMENTS

JP       2001-072750 A     3/2001

* cited by examiner

*Primary Examiner* — Yong Chu
(74) *Attorney, Agent, or Firm* — Panitch Schwarze Belisario & Nadel LLP

(57) ABSTRACT

Disclosed is a method for producing a liquid crystal polyester, which includes the steps of:
(1) polycondensing a mixture of 70.5 to 71.5 mol % of a compound represented by the defined formula (I) (for example, 4-acetoxybenzoic acid) with 28.5 to 29.5 mol % of a compound represented by the defined formula (II) (for example, 6-acetoxy-2-naphthoic acid) to form a prepolymer, wherein the prepolymer has a flow initiation temperature of 200° C. or higher, and the mixture is polycondensed until reaching the temperature which is at least 30° C. lower than the polycondensation temperature; (2) removing the prepolymer in a molten state, followed by solidification and further grinding to produce prepolymer particles; and (3) subjecting the prepolymer particles to a heat treatment at 200 to 310° C. under circulation of an inert gas while remaining in a solid phase state.

6 Claims, No Drawings

METHOD FOR PRODUCING LIQUID CRYSTAL POLYESTER

BACKGROUND OF THE INVENTION

1. Field of the Invention

The present invention relates to a method for producing a liquid crystal polyester.

2. Description of Related Art

JP-A-2001-72750 (corresponding application is US2003-0088053A) discloses, as a method for producing a liquid crystal polyester having a high molecular weight with satisfactory productivity, a method for producing a liquid crystal polyester comprising the steps of (1) polycondensing a monomer in a reaction vessel, (2) removing the formed polymer in a molten state from the reaction vessel and solidifying the polymer, and (3) subjecting the solidified polymer to a solid phase reaction.

However, the liquid crystal polyester obtained by the above production method has such a problem that the molding thereof has unsatisfactory mechanical strength.

SUMMARY OF THE INVENTION

Under such a circumstance, the present invention has been made and an object thereof is to provide a method for producing a liquid crystal polyester, which can produce a liquid crystal polyester having a high molecular weight with satisfactory productivity, a molding of liquid crystal polyester having an improved mechanical strength.

In order to achieve the above object, the present invention provides a method for producing a liquid crystal polyester, which includes the following steps of:

(1) polycondensing a mixture of 70.5 to 71.5 mol % of a compound represented by the formula (I) with 28.5 to 29.5 mol % of a compound represented by the formula (II) (the total of both compounds is 100 mol %) at 260 to 350° C. to form a prepolymer, wherein the prepolymer has a flow initiation temperature of 200° C. or higher, and the mixture is polycondensed until reaching the temperature which is at least 30° C. lower than the polycondensation temperature;

(2) removing the prepolymer in a molten state, followed by solidification and further grinding to produce prepolymer particles having a particle size of 3 mm or less; and (3) subjecting the prepolymer particles to a heat treatment at 200 to 310° C. under circulation of an inert gas while remaining in a solid phase state;

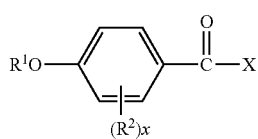
(I)

wherein $R^1$ represents a hydrogen atom, a formyl group, an acetyl group, a propionyl group or a benzoyl group; $R^2$ represents a chlorine atom, a bromine atom, or a group selected from the group consisting of a methyl group, an ethyl group, a propyl group, an isopropyl group, a butyl group, an isobutyl group and a tertiary butyl group; X represents a hydroxy group, an organyloxy group, a halogen atom or an acyloxy group; and X is an integer of 0 to 4 and, when X is 2, 3 or 4, a plurality of $R^2$(s) are the same or different from each other; and

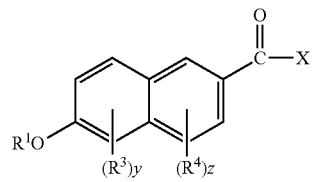
(II)

wherein $R^1$ and X respectively have the same meanings as those of $R^1$ and X in the formula (I), and are respectively the same as or different from each other from $R^1$ and X in the formula (I); $R^3$ and $R^4$ each independently represents a chlorine atom or a group selected from the group consisting of a methyl group, an ethyl group, a propyl group, an isopropyl group, a butyl group, an isobutyl group and a tertiary butyl group; y is an integer of 0 to 3 and, when y is 2 or 3, a plurality of $R^3$(s) are the same or different from each other; and z is an integer of 0 to 3 and, when z is 2 or 3, a plurality of $R^4$(s) are the same or different from each other.

According to the present invention, it is possible to produce a liquid crystal polyester having a high molecular weight and an improved mechanical strength with satisfactory productivity.

EMBODIMENTS OF THE INVENTION

The organyloxy group of X is preferably a methoxy group, an ethoxy group, a propoxy group, a benzyloxy group or a phenoxy group.

In the formula (II), $R^3$ is a group capable of bonding at 5-, 7- or 8-position of a naphthylene group, and $R^4$ is a group capable of bonding at 1-, 3- or 4-position of a naphthylene group.

The flow initiation temperature in the present invention is also called a flow temperature and means a temperature at which a melt viscosity becomes 4,800 Pa·s (48,000 poise) when a liquid crystal polyester is melted while heating at a heating rate of 4° C./min under a load of 9.8 MPa (100 kg/cm²) and extruded through a nozzle having an inner diameter of 1 mm and a length of 10 mm using a capillary rheometer, and the flow initiation temperature serves as an index indicating a molecular weight of the liquid crystal polyester (see "Liquid Crystalline Polymer Synthesis, Molding, and Application" edited by Naoyuki Koide, page 95, published by CMC on Jun. 5, 1987).

Examples of the compound represented by the formula (I) include aromatic carboxylic acids such as 4-hydroxybenzoic acid, 4-formoxybenzoic acid, 4-acetoxybenzoic acid and 4-propionyloxybenzoic acid; and aromatic carboxylic acid esters such as methyl 4-hydroxybenzoate, propyl 4-hydroxybenzoate, phenyl 4-hydroxybenzoate, benzyl 4-hydroxybenzoate, methyl 4-acetoxybenzoate and phenyl 4-acetoxybenzoate. Among these compounds, 4-hydroxybenzoic acid or 4-acetoxybenzoic acid is particularly preferable.

Examples of the derivative of the aromatic hydroxycarboxylic acid other than those mentioned above, which is the compound represented by the formula (I), include acid halides obtained by converting a carboxyl group into a haloformyl group; acid anhydrides obtained by converting a carboxyl group into an acyloxycarbonyl group; and acylates obtained by converting a hydroxyl group into an acyloxy group through acylation.

Examples of the compound represented by the formula (I) further include 3-chloro-4-hydroxybenzoic acid, 2-chloro-4-hydroxybenzoic acid, 2,3-dichloro-4-hydroxybenzoic acid, 3,5-dichloro-4-hydroxybenzoic acid, 2,5-dichloro-4-hydroxybenzoic acid and 3-bromo-4-hydroxybenzoic acid. These compounds can also be used in combination with the above-mentioned compounds for the purpose of improving gas barrier properties of the liquid crystal polyester. These compounds are compounds in which $R^1$ in the formula (I) is a hydrogen atom and X is a hydroxy group, and $R^1$ and X may be other groups defined in the present invention.

The compound represented by the formula (I) to be used in the step (1) may be a combination of a plurality of compounds in which at least one of $R^1$, $R^2$ and X in the formula (I) may be different from each other.

Examples of the compound represented by the formula (II) include aromatic carboxylic acids such as 6-hydroxy-2-naphthoic acid and 6-acetoxy-2-naphthoic acid; and aromatic carboxylic acid esters such as methyl 6-hydroxy-2-naphthoate, phenyl 6-hydroxy-2-naphthoate and methyl 6-acetoxy-2-naphthoate. Among these compounds, 6-hydroxy-2-naphthoic acid or 6-acetoxy-2-naphthoic acid is particularly preferable.

Examples of the derivative of the aromatic hydroxycarboxylic acid other than those mentioned above, which is the compound represented by the formula (II), include acid halides obtained by converting a carboxyl group into a haloformyl group; acid anhydrides obtained by converting a carboxyl group into an acyloxycarbonyl group; and acylates obtained by converting a hydroxyl group into an acyloxyl group through acylation.

Examples of the compound represented by the formula (II) further include 6-hydroxy-5-chloro-2-naphthoic acid, 6-hydroxy-7-chloro-2-naphthoic acid and 6-hydroxy-4,7-dichloro-2-naphthoic acid. These compounds can also be used in combination with the above-mentioned compounds for the purpose of improving gas barrier properties of the liquid crystal polyester. These compounds are compounds in which $R^1$ in the formula (II) is a hydrogen atom and X is a hydroxy group, and $R^1$ and X may be other groups defined in the present invention.

The compound represented by the formula (II) to be used in the step (1) may be a combination of a plurality of compounds in which at least one of $R^1$, $R^3$, $R^4$ and X in the formula (II) may be different from each other.

In the present invention, as long as an important influence is not exerted on physical properties and processability of the obtained liquid crystal polyester, it is possible to use compounds such as 3-hydroxybenzoic acid, 3-formoxybenzoic acid, 3-acetoxybenzoic acid, 3-propionyloxybenzoic acid, methyl 3-hydroxybenzoate, propyl 3-hydroxybenzoate, phenyl 3-hydroxybenzoate, benzyl 3-hydroxybenzoate, methyl 3-acetoxybenzoate, 4'-hydroxybiphenyl-4-carboxylic acid and 4'-acetoxybiphenyl-4-carboxylic acid in combination with compounds represented by the formulas (I) and (II).

The production method of the present invention will be described in detail below every step.

In the step (1), a mixture of a compound represented by the formula (I) with a compound represented by the formula (II) is polycondensed in a reaction vessel. These compounds are charged in the reaction vessel in the form of the mixture, or separately charged in the reaction vessel.

When a compound having a phenolic hydroxyl group (in case $R^1$ is a hydrogen atom) is used as the compound represented by the formula (I) or compound represented by the formula (II), it is preferred to perform the reaction for increasing reactivity of the phenolic hydroxyl group before polycondensation. Examples of the reaction include an acylation reaction of a phenolic hydroxyl group with acid anhydride such as acetic anhydride (for example, acetylation reaction), namely, an esterification reaction between the acid anhydride and the phenolic hydroxyl group. The reaction is performed in (1) a reaction vessel which is different from that for performing polycondensation, or (2) a reaction vessel which is the same as that for performing polycondensation. Among these, an aspect (2) is preferable from the viewpoint of simplicity of an operation capable of still performing polycondensation continuously. In the present invention, the production method is preferably a method in which the compound represented by the formula (I) is 4-acetoxybenzoic acid formed by an acetylation reaction of a phenolic hydroxyl group of 4-hydroxybenzoic acid with acetic anhydride in the step (1), and the compound represented by the formula (II) is 6-acetoxy-2-naphthoic acid formed by an acetylation reaction of a phenolic hydroxyl group of 6-hydroxy-2-naphthoic acid with acetic anhydride in the step (1).

The use amount of the acid anhydride (for example, acetic anhydride) in the above-mentioned esterification reaction is preferably an equivalent amount or more based on the total of the amount of the phenolic hydroxyl group of the compound represented by the formula (I) (for example, 4-hydroxybenzoic acid) and the amount of the phenolic hydroxyl group of the compound represented by the formula (II) (for example, 6-hydroxy-2-naphthoic acid), and more preferably from 1.1 to 1.3 equivalents.

Examples of the material of the reaction vessel for performing the esterification reaction include materials having corrosion resistance, such as titanium and hastelloy B. When the objective liquid crystal polyester is required high color tone (L value), the material of the inner wall of the reaction vessel is preferably glass. Examples of the reaction vessel in which the material of an inner wall is glass include a reaction vessel which is entirely made of glass, and a reaction vessel made of SUS, whose inner wall is glass-lined. Among these reaction vessels, a reaction vessel whose inner wall is glass-lined is preferable in a large-sized production facility. Namely, in the present invention, the step (1) is preferably performed in the reaction vessel whose inner wall is glass-lined.

The polycondensation of the step (1) can be performed in an atmosphere of an inert gas such as nitrogen under the conditions of a normal or reduced pressure. It is particularly preferred that the polycondensation is performed in an inert gas atmosphere under a normal pressure. The polycondensation is performed in a batch-wise or continuous manner or a combination thereof.

The temperature of the polycondensation is from 260 to 350° C., and preferably from 270 to 330° C. When the temperature is lower than 260° C., the polycondensation proceeds slowly. In contrast, when the temperature is higher than 350° C., side reactions such as decomposition of the polymer are likely to occur. When the reaction vessel of the polycondensation of the step (1) is composed of a division divided into multi-stages or partitioned plural divisions and the temperature of the polycondensation of each division is not the same, "polycondensation temperature" in "flow initiation temperature of the prepolymer is at least 30° C. lower than the polycondensation temperature" defined in the present invention means the highest temperature among them.

The time of the polycondensation should be appropriately determined based on other reaction conditions, and is preferably from 0.5 to 5 hours at the temperature of the polycondensation.

The polycondensation sufficiently proceeds even in the absence of a catalyst, but compounds such as (1) oxide and (2) acetate of elements such as Ge, Sn, Ti, Sb, Co and Mn may be optionally used as the catalyst. Use of the catalyst and the kind of the catalyst when used may be determined according to the intended use of the liquid crystal polyester. For example, the liquid crystal polyester to be used in food-related applications is preferably produced in the absence of a catalyst. In the case of the liquid crystal polyester produced by using the catalyst, a catalyst component contained therein must be removed according to the intended use in some cases.

The reaction vessel to be used in the polycondensation may be a reaction vessel having a known shape. In the case of a vertical reaction vessel, the stirring blade is preferably a multi-stage paddle blade, a turbine blade, a monte blade or a double helical blade, and more preferably a multi-stage paddle blade or a turbine blade. A lateral reaction vessel is preferably a reaction vessel provided with a blade having a specific shape, such as a lens blade, an eyeglass blade or an elliptical flat-plate blade in a vertical direction of a single or twin stirring shaft. In order to improve stirring performances and feed mechanism, the blade may be provided with torsion.

The reaction vessel is heated by a heat medium, a gas or an electric heater. In order to uniformly heat a reaction product in the reaction vessel, it is preferred to heat not only the reaction vessel but also members to be immersed in the reaction product, such as a stirring shaft, a blade and a baffle plate.

When the flow initiation temperature of the prepolymer to be formed in the step (1) is lower than 200° C., since the liquid crystal polyesters to be formed are mutually welded or a large amount of by-products are formed in the heat treatment of the step (3), it is not easy to perform the solid phase polymerization and thus it is not preferred from the economic point of view. When the flow initiation temperature of the prepolymer is not at least 30° C. lower than the polycondensation temperature, viscosity of the prepolymer increases and, as a result, (1) it becomes difficult to remove the prepolymer from the reaction vessel and (2) it becomes difficult to stir the reaction vessel, resulting in non-uniform heating of the reaction vessel. Thus, an adverse influence may be exerted on thermostability of the obtained liquid crystal polyester.

The removal of the prepolymer from the reaction vessel in the step (2) is preferably performed in an atmosphere of an inert gas such as a nitrogen gas or an atmosphere of air containing less moisture so as not to cause deterioration of color tone of the obtained liquid crystal polyester. The removal is preferably performed in a state where the atmosphere in the reaction vessel is pressurized within a range from 0.1 to 2 kg/cm$^2$G (gauge pressure), and more preferably from 0.2 to 1 kg/cm$^2$G, using an inert gas such as nitrogen (atmospheric pressure is assumed to be 1.033 kg/cm$^2$A). The removal under pressure enables (1) suppression of the formation of by-products in the step (2), and (2) prevention of shift equilibrium of the polycondensation reaction to the side of the formation of the prepolymer, resulting in suppression of an increase in molecular weight of the prepolymer. As a result, an increase in flow initiation temperature of the prepolymer is suppressed.

Examples of the facility for the removal of the prepolymer in a molten state include an extruder, a gear pump and a valve. After removing the prepolymer for a while, the prepolymer is solidified. Therefore, the solidified prepolymer is ground by a strand cutter or a sheet cutter according to the intended use. Examples of the means for removing a large amount of the prepolymer within a short time, followed by solidification and further grinding include a method of cooling by a double-belt cooler through a weight or volumetric counting feeder described in JP-A-6-256485 or the like.

Examples of the method of cleaning a reaction vessel after the removal of the prepolymer include a method using glycols and/or amines described in JP-A-5-29592 and JP-A-5-29593.

The solidified prepolymer is preferably ground to a particle size of 3 mm or less, more preferably 0.5 mm or less, and more preferably from 0.1 to 0.4 mm, by "grinding" of the step (2) to obtain powdered prepolymer particles. The grinding can be performed using a known grinder. The above-mentioned "size" means the size of particles which pass through (or do not pass through) a sieve having an opening size of the size. For example, "particles having a particle size of 3 mm or less" mean particles which pass through a sieve having an opening size of 3 mm, and "particles having a particle size of 0.1 to 0.4 mm" mean particles which pass through a sieve having an opening size of 0.4 mm and do not pass through a sieve having an opening size of 0.1 mm. When the particle size is more than 3 mm, (1) a difference between the molecular weight of the prepolymer existing in a surface layer of particles and the molecular weight of the prepolymer existing inside particles increases, and thus molecular weight distribution of the whole particles may become wide, and (2) a volatile component in particles is not sufficiently removed, and thus causing foaming and generation of a gas in the step (3). The reason why "difference in molecular weight increases" of the above (1) is that a difference in polymerization rate is caused by a difference in diffusion time of by-products.

The step (3) is the step in which the prepolymer is further allowed to undergo solid phase polymerization by subjecting prepolymer particles to a heat treatment while remaining in a solid phase state under circulation of an inert gas to obtain a prepolymer having increased molecular weight (i.e., liquid crystal polyester). Since the unreacted raw compound (monomer) contained in the prepolymer particles is involved in the solid phase polymerization by the heat treatment, the amount of the raw compound decreases.

The temperature rise rate and maximum treating temperature of the heat treatment are set so that particles of the formed liquid crystal polyester are not welded to each other. Welding is not preferred from the viewpoint of (1) a decrease in surface area of particles of the liquid crystal polyester, (2) a decrease in rate of solid phase polymerization, and (3) a decrease in rate of transpiration of a low boiling point component. The temperature rise rate is preferably from 0.05 to 0.25° C./minute, and more preferably from 0.10 to 0.20° C./minute. The maximum treating temperature is from 200 to 310° C., and preferably from 230 to 300° C. or lower. When the maximum treating temperature is lower than 200° C., the rate of the solid phase polymerization decreases and thus the time of the heat treatment increases, resulting in lack of economy. In contrast, when the maximum treating temperature is higher than 310° C., (1) particles of the liquid crystal polyester may be welded to each other, and (2) the particles may be melted, and thus it is impossible to maintain a solid phase state. The time of the heat treatment is preferably from 1 to 24 hours.

Examples of the device of the heat treatment include various known devices capable of heat-treating a powder, such as a dryer, a reactor, a mixer and an electric furnace. Among these devices, a gas circulating device with high degree of sealing is preferable since a heat treatment can be performed under an inert gas atmosphere.

The above-mentioned inert gas is preferably nitrogen, helium, argon or a carbon dioxide gas, and more preferably nitrogen. The flow rate of the inert gas is determined taking account of factors such as volume of the device of the heat treatment, and particle size and filling state of prepolymer particles, and is usually from 2 to 8 m$^3$/hour, and preferably from 3 to 6 m$^3$/hour, per 1 m$^3$ of the device of the heat treatment. When the flow rate is less than 2 m$^3$/hour, the rate of the solid phase polymerization is slow. In contrast, when the rate is more than 8 m³/hour, scattering of particles may occur in some cases.

The liquid crystal polyester obtained by the production method of the present invention includes 70.5 to 71.5 units of the following repeating unit (A) derived from a compound represented by the formula (I), and 28.5 to 29.5 units of the following repeating unit (B) derived from a compound represented by the formula (II):

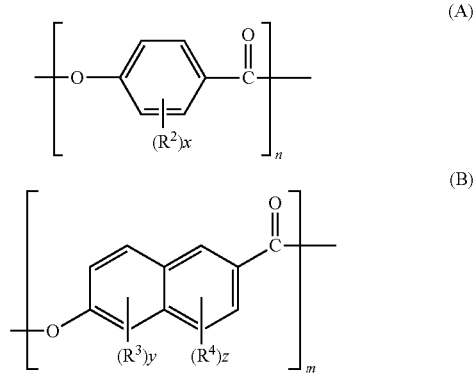

wherein the total of the repeating unit (A) and the repeating unit (B) included in the liquid crystal polyester is 100 units; all symbols described in the repeating units (A) and (B) have the same meanings as those described in the formulas (I) and (II), excluding n and m; n is an integer which denotes the repeating number of repeating unit (A); and m is an integer which denotes the repeating number of repeating unit (B).

The flow temperature of the liquid crystal polyester obtained by the production method of the present invention is preferably from 210 to 320° C., more preferably from 220 to 300° C., and still more preferably from 230 to 280° C. When the flow, temperature is higher than 320° C., the processing temperature of the liquid crystal polyester may be higher than 350° C. in some cases, which is not preferable.

The liquid crystal polyester obtained by the production method of the present invention can be preferably granulated into the form of pellets after melting.

Examples of the method of granulating into pellets include a method in which a liquid crystal polyester is melt-kneaded using a commonly used single- or twin-screw extruder, air-cooled or water cooled and then formed into pellets using a pelletizer (strand cutter). Among commonly used extruders, an extruder with large L/D is preferable so as to uniformly melt and form the liquid crystal polyester. The setting temperature (die head temperature) of a cylinder of the extruder is preferably from 200 to 350° C., more preferably from 230 to 330° C., and still more preferably from 240 to 320° C.

The pellets of the liquid crystal polyester can also be obtained by a method including the following steps of:
(i) removing a prepolymer in a molten state on parallel rollers with a groove, solidifying the prepolymer into a shape of a strand (string), and then cutting the strand (corresponding to grinding) to produce pellet-shaped particles having a particle size of 3 mm or less (corresponding to the above (2)); and
(ii) heat-treating the pellet-shaped prepolymer particles at 200 to 310° C. under circulation of an inert gas while remaining in a solid phase state (corresponding to the above step (3)).

Inorganic fillers can be optionally added to the liquid crystal polyester produced by the production method of the present invention. Examples of inorganic fillers include calcium carbonate, talc, clay, silica, magnesium carbonate, barium sulfate, titanium oxide, alumina, montmorillonite, gypsum, glass flake, glass fiber, carbon fiber, alumina fiber, silica alumina fiber, aluminum borate whisker and potassium titanate fiber. These inorganic fillers can be used as long as transparency and mechanical strength of the molding such as a film made of the liquid crystal polyester are not drastically impaired.

It is also possible to optionally add various additives such as an organic filler, an antioxidant, a heat stabilizer, a photostabilizer, a flame retardant, a lubricant, an antistatic agent, an inorganic or organic colorant, a rust preventing agent, a cross-linking agent, a blowing agent, a fluorescent agent, a surface smoothing agent, a surface gloss improver and a mold release improver (for example, fluororesin) to the liquid crystal polyester produced by the production method of the present invention during the production process of the liquid crystal polyester or after processing process after the production.

According to the present invention, it is possible to produce a liquid crystal polyester having a high molecular weight and an improved mechanical strength with satisfactory productivity.

EXAMPLES

The present invention will be described below by way of Examples, but the present invention is not limited to these Examples. Various physical properties in Examples were measured by the following methods.
1. Flow Initiation Temperature
  Using a flow tester Model CFT-500 manufactured by Shimadzu Corporation, a flow initiation temperature was measured by the following procedure. About 2 g of a liquid crystal polyester was filled in a cylinder with a die including a nozzle having an inner diameter 1 mm and a length of 10 mm attached thereto, and the liquid crystal polyester was extruded through the nozzle while being melted at a temperature rise rate of 4° C./minute under a load of 9.8 MPa (100 kgf/cm²), and then the temperature at which the liquid crystal polyester shows a melt viscosity of 4,800 Pas·s (48,000 poise) was measured and this temperature was regarded as the flow initiation temperature.
2. Tensile Strength
  Using an ASTM No. 4 dumbbell, a tensile strength was measured in accordance with ASTM D638.
3. Bending Strength
  Using a test piece with a size of 13 mm (width), 64 mm (length) and 3 mm (thickness), a bending strength was measured in accordance with ASTM-D790 under the conditions of a bending span distance of 40 mm.
4. Melting Point
  A melting point was measured by a method including the following processes of:
(1) raising the temperature of about 10 mg of pellets from room temperature (about 25° C.) to 320° C. at a rate of 20° C./minute using a differential scanning calorimeter DSC50 manufactured by Shimadzu Corporation;
(2) falling the temperature from 320° C. to 50° C. at a rate of 20° C./minute;
(3) raising the temperature from 50° C. to 320° C. at a rate of 20° C./minute, and measuring an endothermic thermograph; and
(4) regarding the temperature corresponding to an endothermic peak value in the process (3) as the melting point.

5. Generation Amount of Gas

The generation amount of a gas was measured by a method including the following processes of:
(1) producing a No. 1(½) dumbbell (0.8 mm in thickness) defined in JIS K7113;
(2) finely cutting the dumbbell to produce test pieces;
(3) enclosing 5 g of test pieces in a vial (made of glass); and
(4) measuring the amount of a gas generated by heating at 120° C. for 20 hours using a headspace method (measuring method using a gas chromatograph GC-15A manufactured by Shimadzu Corporation, equipped with Head Space Sampler HSS-3A manufactured by Shimadzu Corporation).

Example 1

(1) Formation of Prepolymer

In a 3 liter four-necked separable flask including a Dimorph condenser tube, a distilling head including a nitrogen introducing tube and a thermocouple for the measurement of an inner temperature attached thereto, and an anchor-shaped stirring blade, and also including a thermocouple attached to the outside of the flask, 1176.8 g (8.52 mol, 71.0 mol %) of 4-hydroxybenzoic acid, 654.9 g (3.48 mol) of 6-hydroxy-2-naphthoic acid and 1347.6 g (13.2 mol, 29.0 mol %) of acetic anhydride were charged. Under a nitrogen gas flow, the outer temperature of the flask was raised to 150° C. by a mantle heater and then an acetylation reaction was performed under reflux for about 3 hours while stirring at 200 rpm.

Next, the outer temperature of the flask was raised from 150° C. to 290° C. at a temperature raise rate of 0.6° C./minute. During the temperature rise, acetic acid by-produced by the polycondensation reaction was continuously distilled off. 60 minutes after reaching 290° C., stirring was stopped. The formed prepolymer could be easily removed from the flask in a molten state. The polymer scarcely adhered to the flask and stirring blade. The prepolymer was solidified by being left standing to cool at room temperature. The yield of the prepolymer was 1,565 g (97.8% based on a theoretical yield). It was confirmed by polarizing microscope observation that the prepolymer exhibits optical anisotropy upon melting.

(2) Grinding of Prepolymer

The obtained prepolymer was coarsely ground to a size of about 3-5 cm square, further finely ground using a grinder and then passed through a sieve having an opening size of 2 mm manufactured by Iida Seisakusho Co., Ltd. to obtain particles having a particle size of 2 mm or less of the prepolymer. The particles showed a flow initiation temperature of 231° C.

(3) Solid Phase Polymerization of Prepolymer Particles

Particles of a prepolymer were placed in a tray made of aluminum and the tray was put in a hot-air dryer IPHH-201M manufactured by ESPEC Corp., and then solid phase polymerization was performed by raising the temperature from room temperature to 160° C. over 1 hour under circulation of a nitrogen gas, raising the temperature from 160° C. to 200° C. over 30 minutes, raising the temperature from 200° C. to 260° C. over 7 hours and then maintaining at 260° C. for 5 hours. The particles were removed from the tray which was left standing to cool, to obtain a liquid crystal polyester. The weight of the obtained liquid crystal polyester was 98.5% of the weight of the charged prepolymer. Therefore, a weight loss was 1.5%.

(4) Granulation

The obtained liquid crystal polyester was melt-kneaded at a die head temperature of 280° C. and a screw rotary speed of 150 rpm using a twin-screw extruder PCM-30 manufactured by Ikegai Iron Works, Ltd., and then granulated to obtain pellets. The pellets of the liquid crystal polyester showed a flow initiation temperature of 258° C.

(5) Molding

The obtained pellets were injection-molded at a cylinder temperature of 320° C. and a mold temperature of 130° C. using an injection molding machine PS40E5ASE manufactured by NISSEI PLASTIC INDUSTRIAL CO., LTD. to obtain various test pieces. The test pieces showed a tensile strength of 205 MPa, a bending strength of 108 MPa and a melting point of 280° C. Regarding the generation amount of a gas, the amount of acetic acid was 3.6 ppm and that of phenol was 6.4 ppm.

The results are shown in Table 1.

Comparative Example 1

In the same manner as in Example 1, except that 1176.8 g (8.52 mol, 71.0 mol %) of 4-hydroxybenzoic acid was changed to 1160.2 g (8.4 mol, 70.0 mol %) and 654.9 g (3.48 mol, 29.0 mol %) of 6-hydroxy-2-naphthoic acid was changed to 677.5 g (3.6 mol, 30.0 mol %), respectively, a powdered liquid crystal polyester was obtained.

The obtained liquid crystal polyester included 70.0 units of a repeating unit (A) and 30.0 units of a repeating unit (B). The pellets of the liquid crystal polyester showed a flow initiation temperature of 257° C.

The results are shown in Table 1.

Comparative Example 2

In the same manner as in Example 1, except that 1176.8 g (8.52 mol, 71.0 mol %) of 4-hydroxybenzoic acid was changed to 1209.9 g (8.76 mol, 73.0 mol %) and 654.9 g (3.48 mol, 29.0 mol %) of 6-hydroxy-2-naphthoic acid was changed to 609.7 g (3.24 mol, 27.0 mol %) respectively, a powdered liquid crystal polyester was obtained.

The obtained liquid crystal polyester included 73.0 units of a repeating unit (A) and 27.0 units of a repeating unit (B). The pellets of the liquid crystal polyester showed a flow initiation temperature of 258° C.

The results are shown in Table 1.

Comparative Example 3

In the same manner as in Example 1, except that 1176.8 g (8.52 mol, 71.0 mol %) of 4-hydroxybenzoic acid was changed to 1193.4 g (8.64 mol, 72.0 mol %) and 654.9 g (3.48 mol, 29.0 mol %) of 6-hydroxy-2-naphthoic acid was changed to 632.3 g (3.36 mol, 28.0 mol %) respectively, a powdered liquid crystal polyester was obtained.

The obtained liquid crystal polyester included 72.0 units of a repeating unit (A) and 28.0 units of a repeating unit (B). The pellets of the liquid crystal polyester showed a flow initiation temperature of 258° C.

The results are shown in Table 1.

TABLE 1

|  | Example 1 | Comparative Examples | | |
|---|---|---|---|---|
|  |  | 1 | 2 | 3 |
| Use amount of raw compounds (mol %) |  |  |  |  |
| (1) 4-hydroxybenzoic acid | 71.0 | 70.0 | 73.0 | 72.0 |
| (2) 6-hydroxy-2-naphthoic acid | 29.0 | 30.0 | 27.0 | 28.0 |

TABLE 1-continued

|  | Example 1 | Comparative Examples | | |
|---|---|---|---|---|
|  |  | 1 | 2 | 3 |
| Flow initiation temperature of pellets (° C.) | 258 | 257 | 258 | 258 |
| Tensile strength (MPa) | 205 | 188 | 117 | 190 |
| Bending strength (MPa) | 108 | 104 | 95 | 101 |
| Melting point (° C.) | 280 | 276 | 281 | 279 |
| Generation amount of gas (ppm) |  |  |  |  |
| (1) Acetic acid | 3.6 | 0.8 | 45.2 | 20.4 |
| (2) Phenol | 6.4 | 8.0 | 3.5 | 7.0 |

Based on the above results, the followings can be easily confirmed.

1. When a comparison is made between Example 1, and Comparative Examples 1, 2 and 3, the flow initiation temperature as an indicator of the molecular weight of pellets is almost the same in both. However, the former showed high values as compared with the latter for the tensile strength and bending strength.

2. For the generation amount of a gas (the total amount of acetic acid and phenol) of moldings made from pellets, the amount of Example 1 (10.0 ppm) and that of Comparative Example 1 (8.8 ppm) are almost the same. However, the amount of Example 1 (10.0 ppm) accounted for about ⅕ of that of Comparative Example 2 (48.7 ppm). Also, the amount of Example 1 (10.0 ppm) accounted for about ⅓ of that of Comparative Example 3 (27.4 ppm).

3. For the melting point as an indicator of heat resistance of pellets, the melting point of Example 1 and those of Comparative Examples 2 and 3 are almost the same. However, the melting point of Example 1 was slightly excellent as compared with that of Comparative Example 1.

What is claimed is:

1. A method for producing a liquid crystal polyester, which comprises the following steps of:

(1) polycondensing a mixture of 70.5 to 71.5 mol % of a compound represented by the formula (I) with 28.5 to 29.5 mol % of a compound represented by the formula (II) (the total of both compounds is 100 mol %) at 260 to 350° C. to form a prepolymer, wherein the prepolymer has a flow initiation temperature of 200° C. or higher, and the mixture is polycondensed until reaching the temperature which is at least 30° C. lower than the polycondensation temperature;

(2) removing the prepolymer in a molten state, followed by solidification and further grinding to produce prepolymer particles having a particle size of 3 mm or less; and (3) subjecting the prepolymer particles to a heat treatment at 200 to 310° C. under circulation of an inert gas while remaining in a solid phase state;

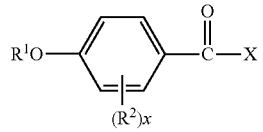

(I)

wherein $R^1$ represents a hydrogen atom, a formyl group, an acetyl group, a propionyl group or a benzoyl group; $R^2$ represents a chlorine atom, a bromine atom, or a group selected from the group consisting of a methyl group, an ethyl group, a propyl group, an isopropyl group, a butyl group, an isobutyl group and a tertiary butyl group; X represents a hydroxy group, an organyloxy group, a halogen atom or an acyloxy group; and X is an integer of 0 to 4 and, when X is 2, 3 or 4, a plurality of $R^2$(s) are the same or different from each other; and

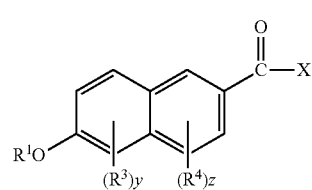

(II)

wherein $R^1$ and X respectively have the same meanings as those of $R^1$ and X in the formula (I), and are respectively the same as or different from each other from $R^1$ and X in the formula (I); $R^3$ and $R^4$ each independently represents a chlorine atom or a group selected from the group consisting of a methyl group, an ethyl group, a propyl group, an isopropyl group, a butyl group, an isobutyl group and a tertiary butyl group; y is an integer of 0 to 3 and, when y is 2 or 3, a plurality of $R^3$(s) are the same or different from each other; and z is an integer of 0 to 3 and, when z is 2 or 3, a plurality of $R^4$(s) are the same or different from each other.

2. The method according to claim 1, wherein the compound represented by the formula (I) is 4-acetoxybenzoic acid, and the compound represented by the formula (II) is 6-acetoxy-2-naphthoic acid.

3. The method according to claim 1, wherein the compound represented by the formula (I) is 4-acetoxybenzoic acid formed by an acetylation reaction of a phenolic hydroxyl group of 4-hydroxybenzoic acid with acetic anhydride in the step (1), and the compound represented by the formula (II) is 6-acetoxy-2-naphthoic acid formed by an acetylation reaction of a phenolic hydroxyl group of 6-hydroxy-2-naphthoic acid with acetic anhydride in the step (1).

4. The method according to claim 3, wherein the charge amount of acetic anhydride is an equivalent amount or more based on the total of the amount of the phenolic hydroxyl group of 4-hydroxybenzoic acid charged and the amount of the phenolic hydroxyl group of 6-hydroxy-2-naphthoic acid charged.

5. The method according to claim 3, wherein the step (1) is performed in a reaction vessel whose inner wall is glass-lined.

6. The method according to claim 1, which includes the step of melting the formed liquid crystal polyester and then granulating the molten liquid crystal polyester after the step (3).

* * * * *